United States Patent
Gobbi et al.

(10) Patent No.: US 7,459,480 B2
(45) Date of Patent: Dec. 2, 2008

(54) BENZODIOXEPINE DERIVATIVES

(75) Inventors: Luca Claudio Gobbi, Oberwil (CH); Marcel Gubler, Arlesheim (CH); Werner Neidhart, Hagenthal le Bas (FR); Matthias Heinrich Nettekoven, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 192 days.

(21) Appl. No.: 10/977,028

(22) Filed: Oct. 29, 2004

(65) Prior Publication Data

US 2005/0113374 A1    May 26, 2005

(30) Foreign Application Priority Data

Nov. 7, 2003    (EP) .................................. 03104117

(51) Int. Cl.
*A61K 31/357* (2006.01)
*C07D 321/10* (2006.01)

(52) U.S. Cl. ...................................... 514/450; 549/350
(58) Field of Classification Search ................. 549/350; 514/450
See application file for complete search history.

(56) References Cited

U.S. PATENT DOCUMENTS 5,420,273 A  5/1995 Klaus et al.
2003/0162818 A1  8/2003 Ikawa et al.
2003/0187254 A1  10/2003 Perry et al.

FOREIGN PATENT DOCUMENTS

EP  0439059  1/1991
EP  1352650  12/2001

OTHER PUBLICATIONS

Balant et al., "Metabolic Considerations, etc.," in Manfred,ed., "Burger's Medicinal Chemistry and Drug Discovery", 5th, vol. 1, NY: John Wiley & Sons, Inc., 1995, 949-982.*
Abu-Elheiga, et. al., Science 291, 2613-2616 (2001).
A.W. Alberts, et. al., The Enzymes, Ed. P.D. Boyer, Academic Press New York (1972) vol. 6, 37-82.
T. Iijima, et. al., Chem. Pharm. Bull (1999) 47, 3, 398-404.
J.D. Mc Garry, et. al., Eur. J. Biochem (1997), 244, 1.
Ruderman, et. al., Am. J. Physiol. 276, E1-E18 (1999).
G.M. Sanders, et. al., Heterocycles (1981) 15, 213-223.

* cited by examiner

*Primary Examiner*—Patricia L Morris
(74) *Attorney, Agent, or Firm*—George W. Johnston; Dennis P. Tramaloni

(57) ABSTRACT

This invention relates to compounds of the formula

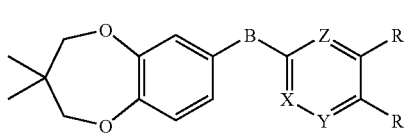

wherein B, X, Y, Z, $R^1$ and $R^2$ are as defined in the description, and pharmaceutically acceptable salts thereof. The invention further relates to pharmaceutical compositions containing such compounds, to a process for their preparation and to their use for the treatment and/or prevention of diseases which are modulated by ACCβ inhibitors.

10 Claims, No Drawings

BENZODIOXEPINE DERIVATIVES

BACKGROUND OF THE INVENTION

Acetyl-Coenzyme A Carboxylases (ACCs, EC 6.4.1.2) catalyze the formation of malonyl-coenzyme A (CoA) and regulate fatty acid biosynthesis and oxidation (A. W. Alberts, P. R. Vagelos in *The Enzymes*, Ed. P. D. Boyer, Academic Press New York 1972, Vol. 6, 37-82). There are two isoforms of ACC in mammals. ACC1 or ACCα is a cytosolic enzyme, and its production of malonyl-CoA is the committed step in the biosynthesis of long-chain fatty acids. In comparison, ACC2 or ACCβ is a mitochondrial enzyme, and its malonyl-CoA product regulates fatty acid oxidation by potently inhibiting the mitochondrial enzyme carnitine palmitoyltransferase I, which transports long-chain acyl-CoAs from the cytosol to the mitochondria for oxidation (J. D. McGarry anf N. F. Brown, Eur. J. Biochem. 1997, 244, 1). Mice lacking ACC2 have a higher than normal rate of fatty acid oxidation and reduced body fat and body weight (L. Abu-Elheiga, M. M. Matzuk, K. A. H. Abo-Hashema, S. J. Wakil, Science 2001, 291, 2613-2616).

ACCβ regulates mitochondrial fatty acid oxidation (Ruderman et al., Am. J. Physiol. 276, E1-E18, 1999) and ACCβ has also been linked to various diseases (Abu-Elheiga et al., Science 291, 2613-2616, 2001). ACC inhibitors seem to be suitable for the use as medicaments, particularly for the treatment and/or prophylaxis of diseases which are related to ACCβ. Furthermore, they can be used for the treatment and/or prophylaxis of diseases which are related to reduced rates of fatty acid oxidation such as obesity, dyslipidemias and diabetes.

SUMMARY OF THE INVENTION

The present invention is concerned with novel benzo[b][1,4]dioxepine derivatives of the general formula

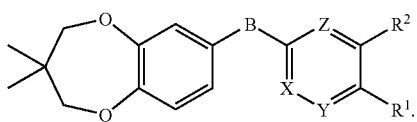

I

The invention further relates to pharmaceutical compositions containing such compounds, to a process for their preparation and to their use for the treatment and/or prevention of diseases which are modulated by ACCβ inhibitors.

DETAILED DESCRIPTION OF THE INVENTION

The present invention is concerned with novel benzo[b][1,4]dioxepine derivatives of the formula

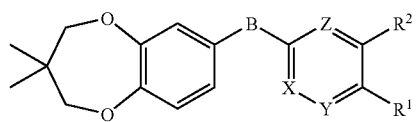

I wherein
B is —C≡C— or —CHR³—O—;
R³ is H or $C_{1-3}$-alkyl;
X, Y and Z are C—R⁴ or N, and at least one of X, Y and Z is C—R⁴;
R⁴ is H or $C_{1-7}$-alkyl;
R¹ and R² are independently from each other selected from the group consisting of
H,
$C_{1-7}$-alkyl,
$C_{1-7}$-alkoxy-$C_{1-7}$-alkyl,
—COOR⁵ or —COR⁵, wherein R⁵ is H or $C_{1-7}$-alkyl,
—OR⁶, wherein R⁶ is H, $C_{1-7}$-alkyl, —(CH₂)$_m$-cycloalkyl, —(CH₂)$_m$-heterocyclyl,
—(CH₂)$_n$—CN, or —(CH₂)$_n$—OR⁷, and R⁷ is H or $C_{1-7}$-alkyl, wherein
m is 0, 1, 2 or 3 and n is 1, 2 or 3;
—SR⁸, wherein R⁸ is H, $C_{1-7}$-alkyl, —(CH₂)$_m$-cycloalkyl, or —(CH₂)$_m$-heterocyclyl,
wherein m is 0, 1, 2 or 3;
—CONR⁹R¹⁰, wherein R⁹ and R¹⁰ are H, $C_{1-7}$-alkyl, or wherein NR⁹R¹⁰ can form a ring having 3 to 7 atoms, said ring optionally including one or more additional N or O atoms,
and a five-membered heteroaromatic ring containing 1 to 4 heteroatoms selected from N, O or S, which is substituted by H or $C_{1-7}$-alkyl;
or R¹ and R² together with the carbon atoms they are attached to can form a ring having 3 to 7 atoms, said ring optionally including one or more N or O atoms;

and pharmaceutically acceptable salts and esters thereof.

It has been found that compounds of formula I are useful as inhibitors of human Acetyl-Coenzyme A Carboxylase (ACC) and further stimulate fatty acid oxidation in liver and muscle, which makes them suitable for the use as medicaments in context with diseases such as e.g. diabetes, obesity and dyslipidemia.

One application relates to metabolic diseases where low levels of fatty acid oxidation in liver are a problem such as e.g. high fatty acid levels in blood, high triglyceride (TG) levels in blood, dyslipidemias in the form of disturbances in the lipoprotein profile, imbalances in very-low-density lipoprotein (VLDL), low-density lipoprotein (LDL) and high-density lipoprotein (HDL), hepatic overproduction of VLDL-bound TG, and vascular diseases associated with the above metabolic abnormalities, comprising atherosclerosis, hypertension and cardiovascular complications.

Thus, ACCβ inhibitors may be useful as medicaments in context with metabolic complications where low levels of fatty acid oxidation in skeletal muscle are a problem such as high TG levels in muscle, elevated levels of reactive fatty acid esters in muscle such as long chain fatty acyl-CoA, carnitine-CoA and diacylglycerol (DAG), low sensitivity or insensitivity of muscle to the action of insulin due to high TG or elevated levels of reactive fatty acid esters in muscle, impaired glucose tolerance as a consequence of reduced insulin sensitivity, progressing stages of low insulin sensitivity resulting in hyperinsulinemia and insulin resistance, further consequences of insulin resistance such as high blood glucose levels (hyperglycemia) and the development of non-insulin-dependent diabetes mellitus (NIDDM, Type 2 diabetes), further consequences caused by hyperglycemia, e.g. diabetic microvascular diseases in the form of nephropathy, neuropathy, retinopathy and blindness.

ACCβ inhibitors can also be used as medicaments in context with medical indications for which increase in fatty acid oxidation is considered beneficial such as obesity syndromes, e.g. excess storage of endogenous lipid (fat), impaired control of appetite and food consumption as a result of low lipid utilization and constant depletion of carbohydrate storage, saving of carbohydrate storage, reduction in the need for carbohydrate supply, suppression of appetite, long term body weight control and maintenance for all persons with genetic, or behavioral inclination to reduced fat oxidation.

Of the diseases mentioned above, the use of compounds of formula (I) as medicaments in context with obesity via increase of mitochondrial fatty acid oxidation in muscle and liver and net increase in energy expenditure in peripheral (muscle) tissue, in context with dyslipidemia via reduced (rebalanced) output by human liver of very low density lipoprotein-bound triglycerides (VLDL-TGs) and in context with insulin resistance and Type II diabetes via reduction in peripheral tissue of high TG levels and reduction of elevated concentrations of the highly reactive esters of fatty acids such as acyl-CoA, carnitine-CoA, diacylglycerol (DAG) are considered to be of particular interest.

Object of the present invention therefore is to provide compounds which must have the criteria mentioned above. It has been found that the compounds of formula (I) of the present invention show the potential to be highly selective ACCβ inhibitors. Subjects of the present invention are further a process for the manufacture of compounds of formula (I) as well as the use of the compounds of formula (I) in the control or prevention of diseases which are mediated by ACCβ inhibitors, and, respectively, their use for the production of corresponding medicaments.

Unless otherwise indicated the following definitions are set forth to illustrate and define the meaning and scope of the various terms used to describe the invention herein.

The term "lower alkyl" or "$C_{1-7}$-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, iso-propyl, n-butyl, s-butyl, t-butyl and the groups specifically exemplified herein.

The term "halogen" refers to fluorine, chlorine, bromine and iodine.

The term "alkoxy" refers to the group R'—O—, wherein R' is alkyl. The term "lower-alkoxy" or "$C_{1-7}$-alkoxy" refers to the group R'—O—, wherein R' is lower-alkyl. Examples of lower-alkoxy groups are e.g. methoxy, ethoxy, propoxy, isopropoxy, butoxy, isobutoxy and hexyloxy. Preferred are the lower-alkoxy groups specifically exemplified herein.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl.

"Heterocyclyl" means a saturated hetrocyclic group, consisting of one or more rings, preferably one to two rings, of three to eight atoms per ring; incorporating one, two, or three ring heteroatoms (chosen from N, O or $S(O)_{0-2}$), which can optionally be mono- or multiply-substituted, particularly mono- or di-substituted by halogen, $CF_3$, lower-alkyl and/or lower-alkoxy. Examples of heterocyclic groups are oxiranyl, morpholinyl, piperazinyl, piperidinyl, pyrrolidinyl, tetrahydropyranyl, thiomorpholinyl, or quinuclidinyl. Preferred are the heterocyclyl groups specifically exemplified herein.

The term "a five-membered heteroaromatic ring containing 1 to 4 heteroatoms selected from N, O or S, which is substituted by H or $C_{1-7}$-alkyl" refers to an aromatic 5- or 6-membered ring which can comprise 1, 2, 3 or 4 atoms selected from nitrogen, oxygen and/or sulphur such as embraces furyl, thienyl, pyrrolyl, imidazolyl, pyrazolyl, oxazolyl, isoxazolyl, thiazolyl, triazolyl, oxadiazolyl, tetrazolyl, oxatriazolyl, pentazolyl and their dihydro derivatives.

The heteroaryl group is optionally substituted by $C_{1-7}$-alkyl. Preferred are the heteroaryl groups specifically exemplified herein.

The term "protecting group" refers to groups such as e.g. acyl, alkoxycarbonyl, aryloxycarbonyl, silyl, or imine-derivatives, which are used to temporarily block the reactivity of functional groups. Well known protecting groups are e.g. lower-alkyl-, β-trimethylsilylethyl- and β-trichloroethyl-esters, which can be used for the protection of carboxy groups.

The term "pharmaceutically acceptable salts" embraces salts of the compounds of formula (I) with pharmaceutically acceptable bases such as alkali salts, e.g. Na- and K-salts, alkaline earth salts, e.g. Ca- and Mg-salts, and ammonium or substituted ammonium salts, such as e.g. trimethylammonium salts. The term "pharmaceutically acceptable salts" also relates to such salts.

The compounds of formula (I) can also be solvated, e.g. hydrated. The solvation can be effected in the course of the manufacturing process or can take place e.g. as a consequence of hygroscopic properties of an initially anhydrous compound of formula (I) (hydration). The term pharmaceutically acceptable salts also includes pharmaceutically acceptable solvates.

The term "pharmaceutically acceptable esters" refers to an in vivo hydrolysable ester of a compound of formula (I) containing an available carboxy group. More particularly, where the group(s) R1 and/or R2 is the group COOR5, in addition to hydrogen or lower alkyl, R5 may be usefully derivatized further to any pharmaceutically acceptable readily hydrolysable moiety.

In detail, the present invention relates to compounds of formula (I)

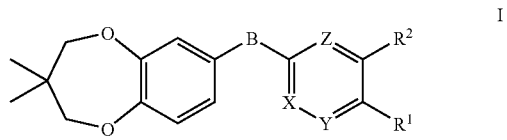

wherein

B is —C≡C— or —$CHR^3$—O—;

$R^3$ is H or $C_{1-3}$-alkyl;

X, Y and Z are C—$R^4$ or N, and at least one of X, Y and Z is C—$R^4$;

$R^4$ is H or $C_{1-7}$-alkyl;

$R^1$ and $R^2$ are independently from each other selected from the group consisting of

H, $C_{1-7}$-alkyl, $C_{1-7}$-alkoxy-$C_{1-7}$-alkyl,

—$COOR^5$ or —$COR^5$, wherein $R^5$ is H or $C_{1-7}$-alkyl,

—$OR^6$, wherein $R^6$ is H, $C_{1-7}$-alkyl, —$(CH_2)_m$-cycloalkyl, —$(CH_2)_m$-heterocyclyl, —$(CH_2)_n$—CN, or —$(CH_2)_n$—$OR^7$, and $R^7$ is H or $C_{1-7}$-alkyl, wherein m is 0, 1, 2 or 3 and n is 1, 2 or 3;

—$SR^8$, wherein $R^8$ is H, $C_{1-7}$-alkyl, —$(CH_2)_m$-cycloalkyl, or —$(CH_2)_m$-heterocyclyl, wherein m is 0, 1, 2 or 3;

—$CONR^9R^{10}$, wherein $R^9$ and $R^{10}$ are H, $C_{1-7}$-alkyl, or wherein $NR^9R^{10}$ can form a ring having 3 to 7 atoms, said ring optionally including one or more additional N or O atoms, and a five-membered heteroaromatic ring containing 1 to 4 heteroatoms selected from N, O or S, which is substituted by H or $C_{1-7}$-alkyl;

or $R^1$ and $R^2$ together with the carbon atoms they are attached to can form a ring having 3 to 7 atoms, said ring optionally including one or more N or O atoms;

and pharmaceutically acceptable salts and esters thereof.

Preferred compounds of formula (I) of the present invention are compounds of formula (I), wherein one of $R^1$ or $R^2$ is hydrogen.

Further preferred are compounds of formula (I), wherein $R^1$ or $R^2$ is selected from the group consisting of
- $C_{1-7}$-alkyl,
- $C_{1-7}$-alkoxy-$C_{1-7}$-alkyl,
- —COOR$^5$, wherein $R^5$ is $C_{1-7}$-alkyl,
- —OR$^6$, wherein $R^6$ is H, $C_{1-7}$-alkyl, —(CH$_2$)$_m$-cycloalkyl, —(CH$_2$)$_m$-heterocyclyl,
- —(CH$_2$)$_n$—CN, or —(CH$_2$)$_n$—OR$^7$, and $R^7$ is H or $C_{1-7}$-alkyl, wherein m is 0, 1, 2 or 3 and n is 1, 2 or 3;
- —SR$^8$, wherein $R^8$ is $C_{1-7}$-alkyl;
- —CONR$^9$R$^{10}$, wherein $R^9$ and $R^{10}$ are H, $C_{1-7}$-alkyl, or wherein NR$^9$R$^{10}$ can form a ring having 3 to 7 atoms, said ring optionally including one or more additional N or O atoms, and a five-membered heteroaromatic ring containing 1 to 4 heteroatoms selected from N, O or S, which is substituted by H or $C_{1-7}$-alkyl.

Especially preferred are compounds of formula (I), wherein $R^1$ or $R^2$ is selected from the group consisting of
- $C_{1-7}$-alkyl,
- $C_{1-7}$-alkoxy-$C_{1-7}$-alkyl,
- —COOR$^5$, wherein $R^5$ is H or $C_{1-7}$-alkyl,
- —OR$^6$, wherein $R^6$ is H, $C_{1-7}$-alkyl, —(CH$_2$)$_m$-cycloalkyl, —(CH$_2$)$_m$-heterocyclyl,
- —(CH$_2$)$_n$—CN, or —(CH$_2$)$_n$—OR$^7$, and $R^7$ is H or $C_{1-7}$-alkyl, wherein m is 0, 1, 2 or 3 and n is 1, 2 or 3; and
- —SR$^8$, wherein $R^8$ is $C_{1-7}$-alkyl.

More preferred are those compounds of formula (I) in accordance with the present invention, wherein $R^1$ or $R^2$ is —COOR$^5$, and $R^5$ is H or $C_{1-7}$-alkyl.

Furthermore, compounds of formula (I) are preferred, wherein $R^1$ or $R^2$ is selected from the group consisting of $C_{1-7}$-alkoxy-$C_{1-7}$-alkyl, —OR$^6$, wherein $R^6$ is H, $C_{1-7}$-alkyl, —(CH$_2$)$_m$-cycloalkyl, —(CH$_2$)$_m$-heterocyclyl, —(CH$_2$)$_n$—CN, or —(CH$_2$)$_n$—OR$^7$, and $R^7$ is H or $C_{1-7}$-alkyl, wherein m is 0, 1, 2 or 3 and n is 1, 2 or 3; and —SR$^8$, wherein $R^8$ is $C_{1-7}$-alkyl.

Also preferred are compounds of formula (I), wherein $R^1$ or $R^2$ is a five-membered heteroaromatic ring containing 1 to 4 heteroatoms selected from N, O or S, which is substituted by H or $C_{1-7}$-alkyl.

Compounds of formula (I) according to the present invention, wherein $R^1$ and $R^2$ together with the carbon atoms they are attached to form a ring having 3 to 7 atoms, said ring optionally including one or more N or O atoms, are also preferred.

Further preferred are compounds of formula (I) having the formula

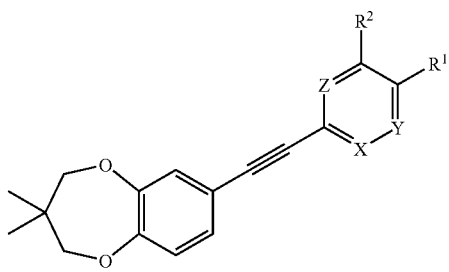

I-A wherein
X, Y, Z, $R^1$ and $R^2$ are as defined in claim 1; and
pharmaceutically acceptable salts and/or esters thereof.

Especially preferred are those compounds of formula (I-A), wherein X, Y und Z are
—CR$^4$ and $R^4$ is hydrogen.

Examples of such compounds are the following:
4-(3,3-dimethyl-3,4-dihydro-2H-benzo[b][1,4]dioxepin-7-ylethynyl)-benzoic acid ethyl ester;
3-(3,3-dimethyl-3,4-dihydro-2H-benzo[b][1,4]dioxepin-7-ylethynyl)-benzoic acid ethyl ester;
3,3-dimethyl-7-(4-methylsulfanyl-phenylethynyl)-3,4-dihydro-2H-benzo[b][1,4]dioxepine;
7-(4-methoxy-phenylethynyl)-3,3-dimethyl-3,4-dihydro-2H-benzo[b][1,4]dioxepine;
4-(3,3-dimethyl-3,4-dihydro-2H-benzo[b][1,4]dioxepin-7-ylethynyl)-phenol;
7-(4-ethoxy-phenylethynyl)-3,3-dimethyl-3,4-dihydro-2H-benzo[b][1,4]dioxepine;
7-(4-ethoxymethyl-phenylethynyl)-3,3-dimethyl-3,4-dihydro-2H-benzo[b][1,4]dioxepine;
2-[4-(3,3-dimethyl-3,4-dihydro-2H-benzo[b][1,4]dioxepin-7-ylethynyl)-phenyl]-5-methyl-[1,3,4]oxadiazole;
7-(4-cyclopropylmethoxy-phenylethynyl)-3,3-dimethyl-3,4-dihydro-2H-benzo[b][1,4]dioxepine;
3,3-dimethyl-7-(4-propoxy-phenylethynyl)-3,4-dihydro-2H-benzo[b][1,4]dioxepine; and
3,3-dimethyl-7-(4-oxiranylmethoxy-phenylethynyl)-3,4-dihydro-2H-benzo[b][1,4]dioxepine.

Also preferred are compounds of formula (I-A), wherein one of X, Y or Z is N and the others are —CR$^4$ and $R^4$ is hydrogen.

The following compounds are examples thereof:
6-(3,3-dimethyl-3,4-dihydro-2H-benzo[b][1,4]dioxepin-7-ylethynyl)-nicotinic acid ethyl ester; and
5-(3,3-dimethyl-3,4-dihydro-2H-benzo[b][1,4]dioxepin-7-ylethynyl)-pyridine-2-carboxylic acid ethyl ester.

Furthermore, compounds of formula (I) having the formula

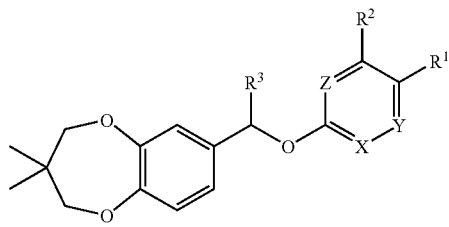

I-B wherein
X, Y, Z, R¹, R² and R³ are as defined in claim 1; and pharmaceutically acceptable salts and/or esters thereof, are also preferred.

Particularly preferred are compounds of formula (I-B), wherein X, Y und Z are —CR⁴ and R⁴ is hydrogen.

Examples of such compounds are the following:
4-(3,3-dimethyl-3,4-dihydro-2H-benzo[b][1,4]dioxepin-7-ylmethoxy)-benzoic acid ethyl ester; and
7-(3-ethoxy-phenoxymethyl)-3,3-dimethyl-3,4-dihydro-2H-benzo[b][1,4]dioxepine.

Furthermore, the following compounds are examples of preferred compounds of the present invention:
4-(3,3-dimethyl-3,4-dihydro-2H-benzo[b][1,4]dioxepin-7-ylethynyl)-benzoic acid ethyl ester;
3-(3,3-dimethyl-3,4-dihydro-2H-benzo[b][1,4]dioxepin-7-ylethynyl)-benzoic acid ethyl ester;
3,3-dimethyl-7-(4-methylsulfanyl-phenylethynyl)-3,4-dihydro-2H-benzo[b][1,4]dioxepine;
1-[4-(3,3-dimethyl-3,4-dihydro-2H-benzo[b][1,4]dioxepin-7-ylethynyl)-phenyl]-ethanone;
7-(4-methoxy-phenylethynyl)-3,3-dimethyl-3,4-dihydro-2H-benzo[b][1,4]dioxepine;
7-(3-methoxy-phenylethynyl)-3,3-dimethyl-3,4-dihydro-2H-benzo[b][1,4]dioxepine;
4-(3,3-dimethyl-3,4-dihydro-2H-benzo[b][1,4]dioxepin-7-ylethynyl)-phenol;
7-(4-ethoxy-phenylethynyl)-3,3-dimethyl-3,4-dihydro-2H-benzo[b][1,4]dioxepine;
7-benzo[1,3]dioxol-5-ylethynyl-3,3-dimethyl-3,4-dihydro-2H-benzo[b][1,4]dioxepine;
7-(2,3-dihydro-benzofuran-5-ylethynyl)-3,3-dimethyl-3,4-dihydro-2H-benzo[b][1,4]dioxepine;
[4-(3,3-dimethyl-3,4-dihydro-2H-benzo[b][1,4]dioxepin-7-ylethynyl)-phenyl]-morpholin-4-yl-methanone;
4-(3,3-dimethyl-3,4-dihydro-2H-benzo[b][1,4]dioxepin-7-ylethynyl)-N,N-dimethyl-benzamide;
6-(3,3-dimethyl-3,4-dihydro-2H-benzo[b][1,4]dioxepin-7-ylethynyl)-nicotinic acid ethyl ester;
7-(4-ethoxymethyl-phenylethynyl)-3,3-dimethyl-3,4-dihydro-2H-benzo[b][1,4]dioxepine;
2-[4-(3,3-dimethyl-3,4-dihydro-2H-benzo[b][1,4]dioxepin-7-ylethynyl)-phenyl]-5-[1,3,4]methyl-oxadiazole;
5-(3,3-dimethyl-3,4-dihydro-2H-benzo[b][1,4]dioxepin-7-ylethynyl)-pyridine-2-carboxylic acid ethyl ester;
4-(3,3-dimethyl-3,4-dihydro-2H-benzo[b][1,4]dioxepin-7-ylmethoxy)-benzoic acid ethyl ester;
7-(4-cyclopropylmethoxy-phenylethynyl)-3,3-dimethyl-3,4-dihydro-2H-benzo[b][1,4]dioxepine;
7-[4-(2-methoxy-ethoxy)-phenylethynyl]-3,3-dimethyl-3,4-dihydro-2H-benzo[b][1,4]dioxepine;
[4-(3,3-dimethyl-3,4-dihydro-2H-benzo[b][1,4]dioxepin-7-ylethynyl)-phenoxy]-acetonitrile;
3,3-dimethyl-7-(4-propoxy-phenylethynyl)-3,4-dihydro-2H-benzo[b][1,4]dioxepine;
3,3-dimethyl-7-(4-oxiranylmethoxy-phenylethynyl)-3,4-dihydro-2H-benzo[b][1,4]dioxepine;
7-(4-isopropyl-phenoxymethyl)-3,3-dimethyl-3,4-dihydro-2H-benzo[b][1,4]dioxepine;
3,3-dimethyl-7-(4-methylsulfanyl-phenoxymethyl)-3,4-dihydro-2H-benzo[b][1,4]dioxepine;
7-(3-ethoxy-phenoxymethyl)-3,3-dimethyl-3,4-dihydro-2H-benzo[b][1,4]dioxepine;
7-(4-ethyl-phenoxymethyl)-3,3-dimethyl-3,4-dihydro-2H-benzo[b][1,4]dioxepine;
7-(4-methoxy-phenoxymethyl)-3,3-dimethyl-3,4-dihydro-2H-benzo[b][1,4]dioxepine; and
5-[4-(3,3-dimethyl-3,4-dihydro-2H-benzo[b][1,4]dioxepin-7-ylethynyl)-phenyl]-2-methyl-2H-tetrazole.

The pharmaceutically acceptable salts of the compounds of formula (I) also constitute preferred embodiments of the present invention.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula (I) in vivo are also within the scope of this invention.

A further aspect of the present invention is the process for the manufacture of compounds of formula (I) as defined above, which process comprises reacting a compound of formula

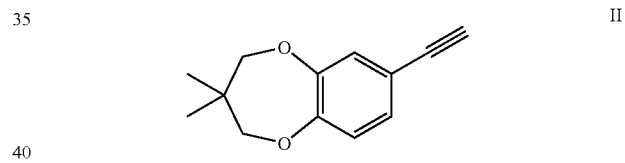

II with an aryl halide or heteroaryl halide of formula

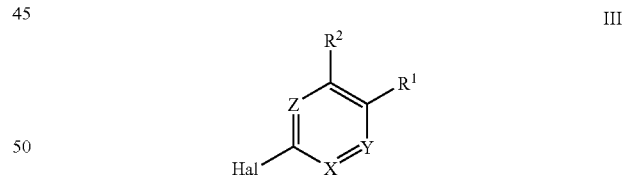

III wherein Hal is bromide or iodide and X, Y, Z, R¹ and R² are as defined herein before, to obtain a compound of formula

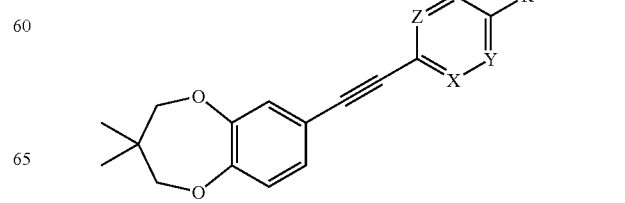

I-A wherein X, Y, Z, R$^1$ and R$^2$ are as defined herein before, or, alternatively, reacting a compound of formula

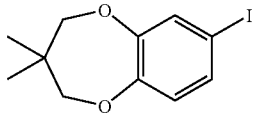

IV with an alkine of formula

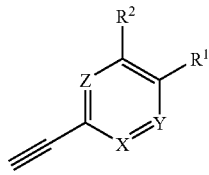

V wherein X, Y, Z, R$^1$ and R$^2$ are as defined herein before, to obtain a compound of formula

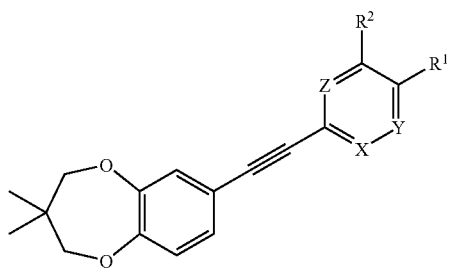

I-A wherein X, Y, Z, R$^1$ and R$^2$ are as defined herein before, or, alternatively, reacting a compound of formula

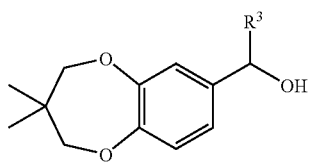

VI wherein R$^3$ is H or C$_{1-3}$-alkyl, with a compound of formula

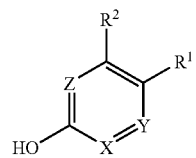

VII wherein X, Y, Z, R$^1$ and R$^2$ are as defined before, to obtain a compound of formula

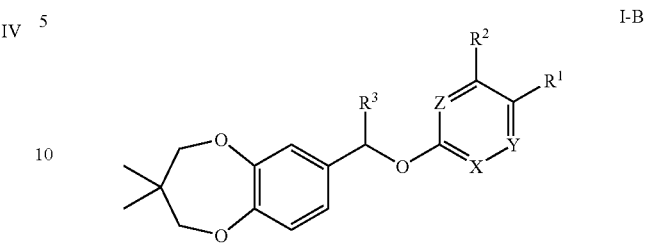

I-B wherein X, Y, Z, R$^1$, R$^2$ and R$^3$ are as defined before.

As described above, the compounds of formula (I) of the present invention can be used as medicaments for the treatment and/or prevention of diseases which are associated with ACCβ and/or fatty acid oxidation, such as e.g. diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, and dyslipidemia. The use as medicament for the treatment and/or prevention of diabetes, especially non insulin dependent diabetes mellitus, obesity and dyslipidemia is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are modulated by ACCβ inhibitors. Examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, obesity and dyslipidemia.

In another embodiment, the invention relates to a method for the treatment and/or prevention of diseases which are modulated by ACCβ inhibitors, which method comprises administering a compound of formula (I) to a human or animal. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, obesity and dyslipidemia. A preferred method as defined above is one, wherein the diesease is diabetes, more preferably non insulin dependent diabetes mellitus, obesity or dyslipidemia.

The invention further relates to the use of compounds as defined above for the treatment and/or prevention of diseases which are modulated by ACCβ inhibitors. Preferred examples of such diseases diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, obesity and dyslipidemia. In a preferred embodiment, the present invention relates to the use as defined above, wherein the disease is diabetes, preferably non insulin dependent diabetis mellitus, obesity or dyslipidemia.

In addition, the invention relates to the use of compounds as defined above for the preparation of medicaments for the treatment and/or prevention of diseases which are modulated by ACCβ inhibitors. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, obesity and dyslipidemia. Such medicaments comprise a compound as defined above.

The compounds of formula (I) can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

Compounds of formula (I) wherein B is —C≡C— (acetylene derivatives) are prepared by a Sonogashira cross coupling reaction of an appropriate aryl iodide or bromide with trimethylsilylacetylene followed by a TMS deprotection and a second Sonogashira reaction (general conditions for the cross coupling step: [PdCl$_2$(PPh$_3$)$_2$], CuI, iPr$_2$NH, THF, heat).

The synthesis of the key aryl iodide (5) is shown in Scheme 1.

7-Iodo-3,3-dimethyl-3,4-dihydro-2H-benzo[b][1,4]dioxepine (5) is obtained by iodination of 3,3-dimethyl-3,4-dihydro-2H-benzo[b][1,4]dioxepine (4) with silver trifluoroacetate in CH$_2$Cl$_2$. 3,3-dimethyl-3,4-dihydro-2H-benzo[b][1,4]dioxepine (4) is prepared according to M. Klaus, P. Mohr, E. Weiss, Eur. Pat. Appl. EP 0 350 846 A2 (1990).

Most examples are prepared from the advanced acetylenic intermediate (6), obtained from iodide 5) by cross coupling with trimethylsilylacetylene and subsequent cleavage of the TMS moiety with K$_2$CO$_3$ in THF/MeOH (Scheme 2). In a second Sonogashira cross coupling reaction (6) is reacted with an appropriate aryl halide or heteroaryl halide of type (7) to obtain a compound of formula (I-A).

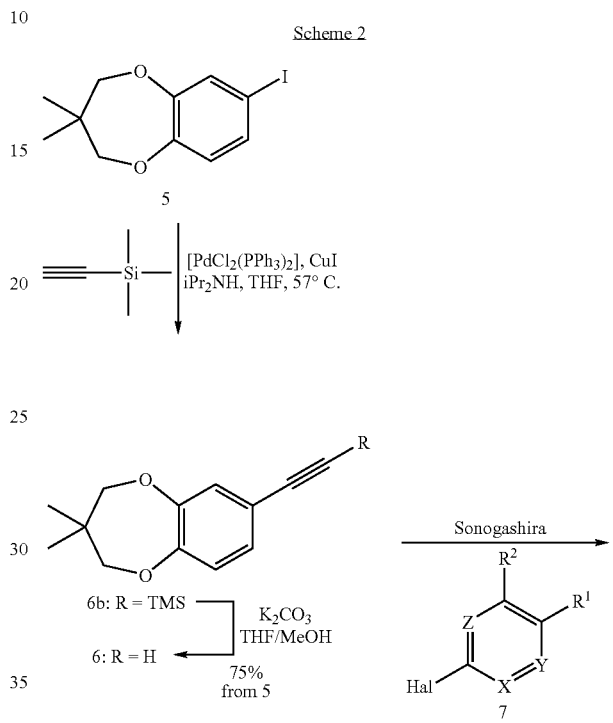

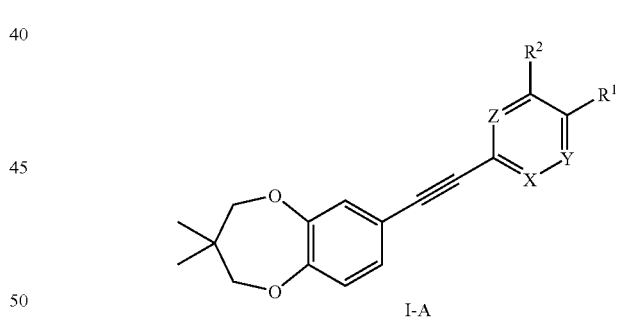

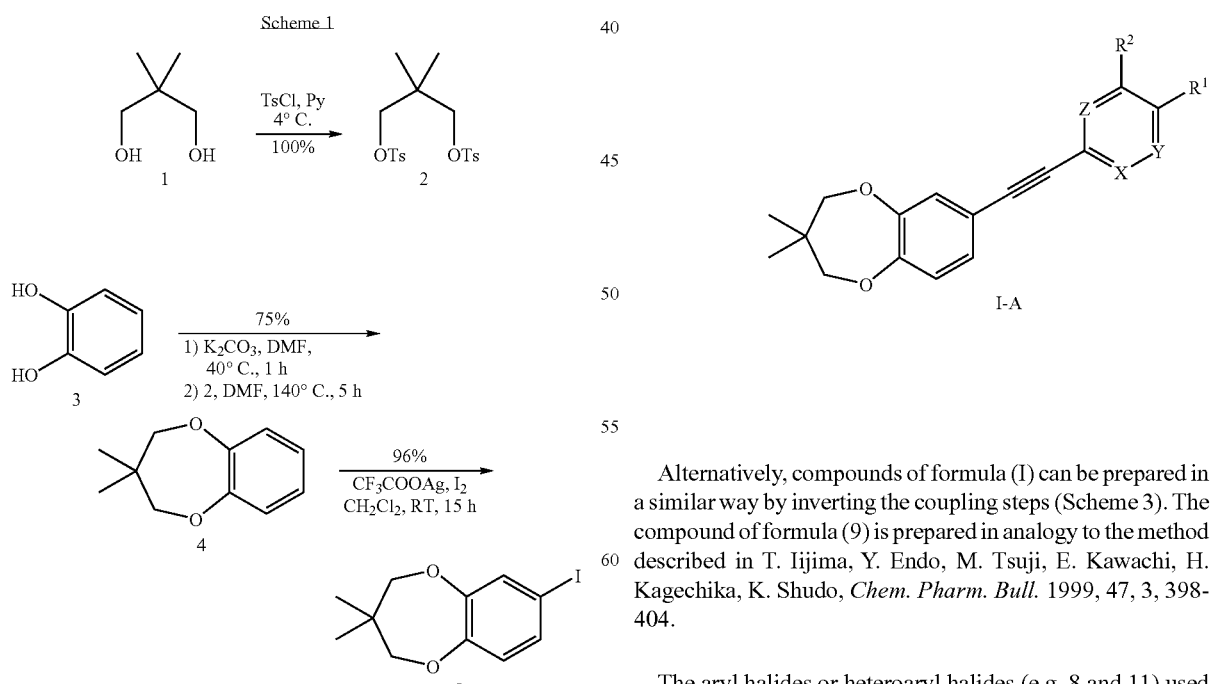

Alternatively, compounds of formula (I) can be prepared in a similar way by inverting the coupling steps (Scheme 3). The compound of formula (9) is prepared in analogy to the method described in T. Iijima, Y. Endo, M. Tsuji, E. Kawachi, H. Kagechika, K. Shudo, Chem. Pharm. Bull. 1999, 47, 3, 398-404.

The aryl halides or heteroaryl halides (e.g. 8 and 11) used as starting material are commercially available or can be prepared as follows.

Amides of type (12) are obtained from the reaction of 4-iodobenzoyl chloride (11) and the corresponding amines in CH$_2$Cl$_2$ and Et$_3$N.

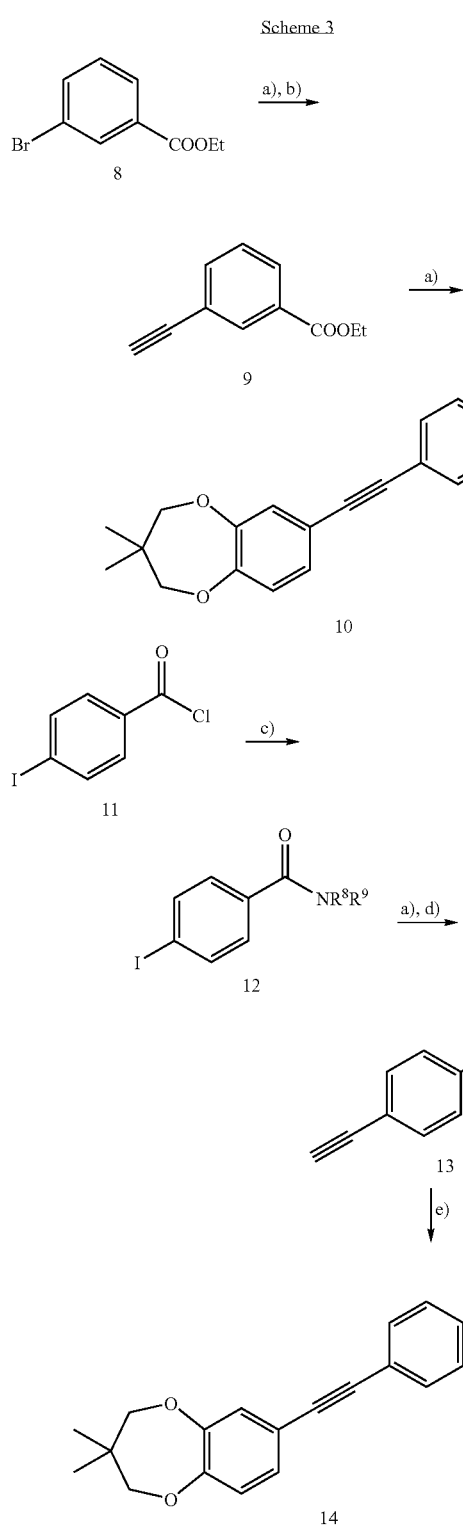

a) [PdCl$_2$(PPh$_3$)$_2$], CuI, i-Pr$_2$NH, THF, 57° C., Me$_3$Si—≡
b) K$_2$CO$_3$, EtOH/THF
c) Amine, Et$_3$N, CH$_2$Cl$_2$
d) K$_2$CO$_3$, MeOH/THF
e) [PdCl$_2$(PPh$_3$)$_2$], CuI, i-Pr$_2$NH, THF, 57° C.

Bromide (16) is obtained from 4-bromobenzyl bromide (15) in refluxing ethanol (see Scheme 4).

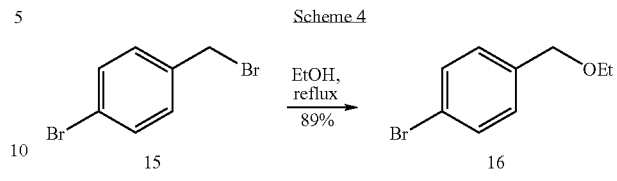

1,3,4-Oxadiazole (19) is obtained from reaction of 4-iodobenzoic acid (17) and acethydrazide (18) in phosphoryl chloride (POCl$_3$) at 100° C. (see Scheme 5).

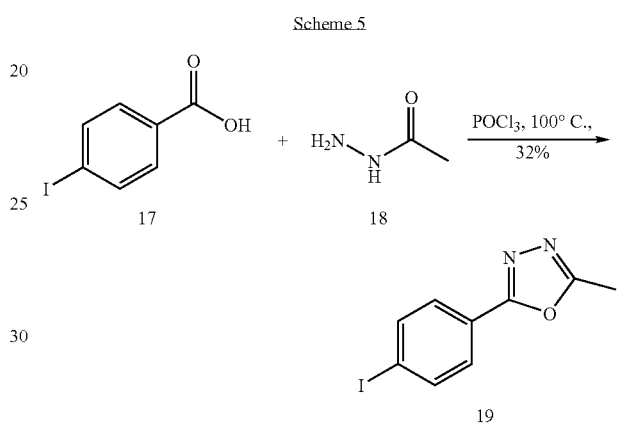

Pyridine (22) is obtained in two steps from 5-bromo-2-methyl-pyridine (20) by oxidation to 5-bromo-2-pyridinecarboxylic acid (21) as described in G. M. Sanders, M. van Dijk and H. C. van der Plas, *Heterocycles* 1981, 15, 213-223, and chlorination with SOCl$_2$ followed by reaction with EtOH (see Scheme 6).

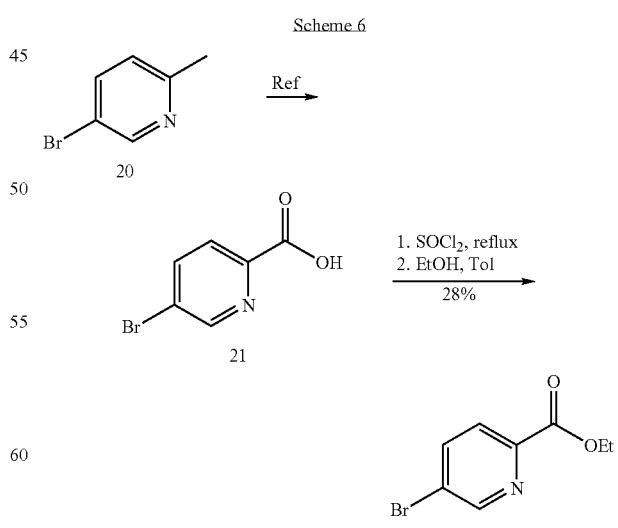

Reaction of 4-iodobenzonitrile (23) with sodium azide affords tetrazole (24) that can be methylated to a mixture of 25/26. The two regioisomers are easily separated by flash chromatography (see Scheme 7).

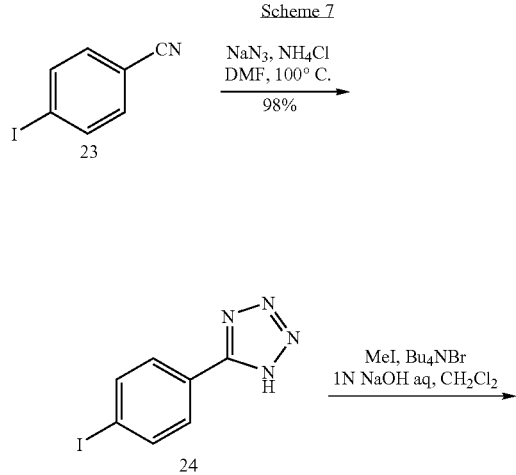

Compounds of formula (I) of the present invention, wherein $R^1$ is —$OR^5$ and $R^5$ is $C_{1-7}$-alkyl, —$(CH_2)_n$-cycloalkyl, —$(CH_2)_n$-heterocyclyl, —$(CH_2)_n$—CN, or —$(CH_2)_n$—$OR^6$, and $R^6$ is H or $C_{1-6}$-alkyl, can be obtained by alkylation of the corresponding phenol (27) (see Scheme 8).

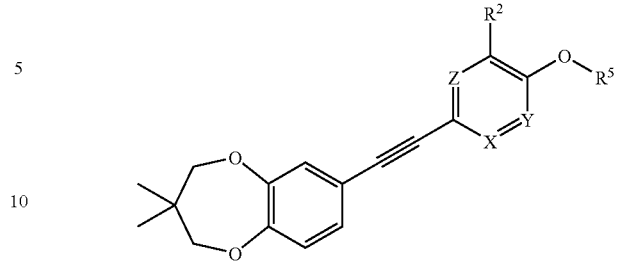

Compounds of formula (I) wherein B is —$CH_2O$— (benzylether derivatives) are prepared by alkylation of alcohol (31) under Mitzunobu conditions (see Scheme 9). Ester (30) is obtained from ethyl 3,4-dihydroxybenzoate following a similar procedure to the synthesis of (4) (M. Klaus, P. Mohr, E. Weiss, Eur. Pat. Appl. EP 0 350 846 A2). Reduction of (30) with DIBAL-H affords alcohol (31).

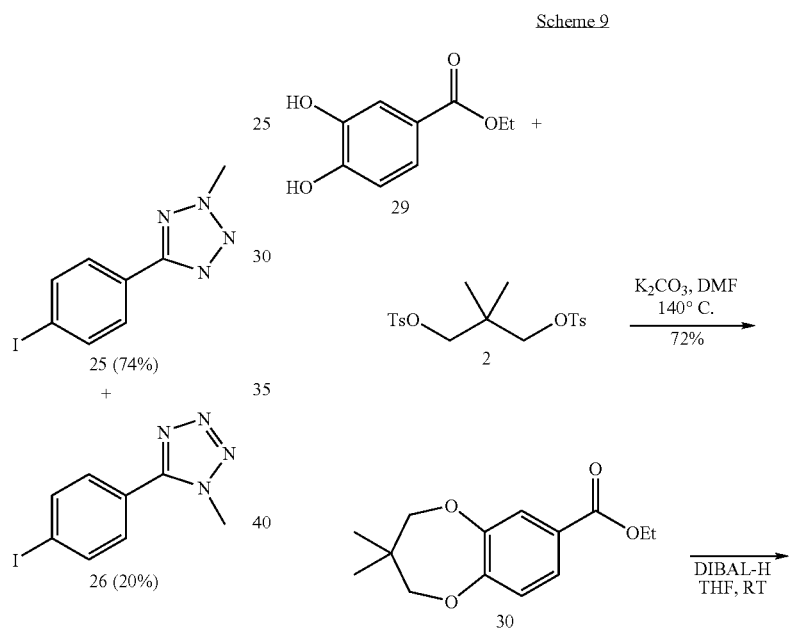

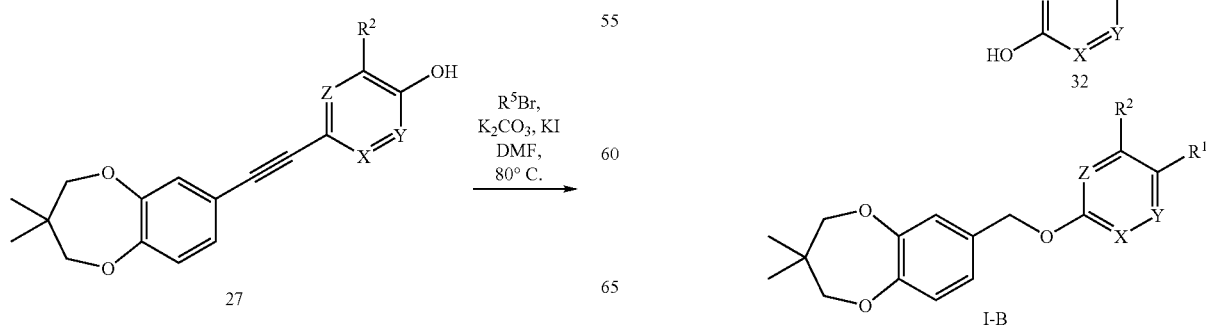

It will be appreciated, that the compounds of general formula (I) of this invention may be derivatised at functional groups to provide derivatives which are capable of conversion back to the parent compound in vivo.

The following test was carried out in order to determine the activity of the compounds of formula (I):

Production and Characterization of Human ACCβ Enzyme, Its Use in ACC Activity Assays and for Inhibition Studies The cloning of the full length human muscle-type ACCβ cDNA and expression in HEK293 cells (ATCC, # CRL-1573) was performed as follows. The ACCβ cDNA was amplified by the polymerase chain reaction (PCR) and was cloned using standard recombinant DNA techniques. The PCR reaction was performed with the Expand Long Template PCR System (Roche Molecular Biochemicals, # 1 681 8340) and 0.5 ng of cDNA from human skeletal muscle as template. The primers used for PCR amplification were designed on the basis of the published sequence of the human ACCβ cDNA isolated from a human liver cDNA library (Abul-Elheiga et al. J. Biol. Chem. 272, 10669-10677, 1997). The sequence of the forward primer ACCB1 was 5'-TTACGCGTGCTAGCCAC-CATGGTCTTGCTTCTTTGTCTATC-3'; it includes a NheI restriction cleavage site for subcloning and a Kozak translation initiation consensus sequence preceding the ATG start codon. The sequence of the reverse primer ACCB8 was 5'-TTCTCGAGTCAGGTGGAGGCCGGGCTGTC-3'; it includes a stop codon and a XhoI restriction cleavage site for subcloning. The amplified DNA fragment of approximately 7.4 kb was cloned into a mammalian expression vector. The resulting plasmid isolates, pRF33A, B, C, D, and E were individually transfected in human embryonic kidney 293 cells (HEK293) using a standard lipid transfection method. Cell extracts of transfected cells were prepared in a lysis buffer containing 0.4 mg/ml digitonin and enzyme activity was determined using a radiometric ACC activity assay as described below. Plasmid pRF33D gave the highest activity and was chosen for large scale transfections of HEK293 cells and enzyme purification.

Since ACC enzyme activities in crude cell lysates were very low, enrichment of ACCβ enzyme expressed in HEK293 cells was achieved by a single anion exchange chromatography step. Cell lysates were run over a 5 ml Econo Pac High Q column (Bio-Rad, # 732-0027). Bound proteins were eluted by a gradient of NaCl from 0 to 1 M in 50 mM Tris-HCl, pH 7.5, 1 mM DTT, 5% glycerol. Fractions containing high ACCβ enzyme activity were pooled and stored at −20° C.

Standard ACCβ enzyme assays, in a total volume of 100 µl, contained 50 mM HEPES-KOH, pH 7.5, 10 mM K-citrate, 10 mM $MgSO_4$, 1 mM ATP, 0.1 mM DTT, 2% DMSO, 0.1 mg/ml fatty acid-free BSA, 0.2 mM acetyl-CoA, 2 mM $KHCO_3$, 0.2 mM [$^{14}$C]$NaHCO_3$ (50-60 mCi/mmol) and cell lysate or purified ACCβ enzyme. Reactions were incubated at 37° C. for 45 min. and stopped by the addition of 50 µl of 2 N HCl. Terminated reactions were incubated at 50° C. over night to evaporate non-incorporated [$^{14}$C]$NaHCO_3$. [$^{14}$C]-labeled malonyl-CoA reaction product was quantitated by liquid scintillation counting after the addition of 20 µl of Microscint 20 (Canberra Packard, # 6013621) on a TopCount NXT microplate scintillation counter (Canberra Packard).

Inhibition of ACCβ activity was determined at saturating substrate concentrations with two-fold serial dilutions of test compounds spanning a concentration range of at least two log units. $IC_{50}$ values were calculated with the GraFit software (Erithacus Software Ltd.).

The preferred compounds of the present invention exhibit $IC_{50}$ values of 5 nM to 100 µM, preferably 1 to 1000 nM.

The following table shows measured values for some selected compounds of the present invention.

|  | ACCβ $IC_{50}$ (µmol/l) |
| --- | --- |
| Example 5 | 42.2 |
| Example 7 | 1.44 |
| Example 9 | 15.1 |
| Example 13 | 5.41 |
| Example 14 | 11.2 |
| Example 15 | 3.11 |
| Example 21 | 0.01 |
| Example 23 | 0.25 |

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula (I).

The following examples serve to illustrate the present invention in more detail. They are, however, not intended to limit its scope in any manner.

EXAMPLES

Example 1

4-(3,3-Dimethyl-3,4-dihydro-2H-benzo[b][1,4]dioxepin-7-ylethynyl)-benzoic acid ethyl ester 3,3-Dimethyl-3,4-dihydro-2H-benzo[b][1,4]dioxepine (4)

The title compound was prepared according to the method as described in M. Klaus, P. Mohr, E. Weiss, Eur. Pat. Appl. EP 0 350 846 A2 (1990).

7-Iodo-3,3-dimethyl-3,4-dihydro-2H-benzo[b][1,4]dioxepine (5)

A solution of 3,3-dimethyl-3,4-dihydro-2H-benzo[b][1,4]dioxepine (4) (726 mg) in $CH_2Cl_2$ (40 ml) is prepared and silver trifluoroacetate (1.13 g) and iodine (1.06 g) are subsequently added. Precipitation of silver iodide is immediately observed. The mixture is stirred 16 h before filtration over dicalite. The organic layer is washed with sat. aq. $Na_2O_3S_2$ sol. (2×50 ml) and water (2×50 ml). The aqueous layers are extracted one more time with $CH_2Cl_2$ (50 ml). After drying ($MgSO_4$) the solvent is evaporated yielding 7-iodo-3,3-dimethyl-3,4-dihydro-2H-benzo[b][1,4]dioxepine (5) as a light brown oil, MS (ESI) 304.1 $(M)^+$.

(3,3-Dimethyl-3,4-dihydro-2H-benzo[b][1,4]dioxepin-7-ylethynyl)-trimethyl-silane (6b)

To a mixture of $[PdCl_2(PPh_3)_2]$ (1.73 g) and copper(I) iodide (845 mg) under Ar is added a degassed solution of 7-iodo-3,3-dimethyl-3,4-dihydro-2H-benzo[b][1,4]dioxepine (7) (15.0 g) in diisopropylamine (225 ml) and THF (225 ml). Trimetylsilylacetylene (7.27 g) is added and the mixture is stirred over night at 57° C. After addition of AcOEt (1 L) and filtration over dicalite, the solution is washed with 1 N aq. HCl sol. (3×1 L) and brine (2×1 L). The organic layer is dried over $Na_2SO_4$ and the solvent is evaporated to yield (3,3-dimethyl-3,4-dihydro-2H-benzo[b][1,4]dioxepin-7-ylethynyl)-trimethyl-silane (6b) as a brown oil.

7-Ethynyl-3,3-dimethyl-3,4-dihydro-2H-benzo[b][1,4]dioxepine (6)

All material from step c) is dissolved in THF (200 ml) and MeOH (1 L) and $K_2CO_3$ (3.98 g) are added. The mixture is stirred 1 h at RT, diluted with $Et_2O$ (1.2 L) and extracted with $H_2O$ (2×500 ml). After drying over $Na_2SO_4$ the solvent is evaporated to obtain 8.7 g of 7-ethynyl-3,3-dimethyl-3,4-dihydro-2H-benzo[b][1,4]dioxepine (6) as a dark brown oil, MS (ESI) 202.2 $(M^{\bullet})^+$.

4-(3,3-Dimethyl-3,4-dihydro-2H-benzo[b][1,4]dioxepin-7-ylethynyl)-benzoic acid ethyl ester To a mixture under Ar of 7-ethynyl-3,3-dimethyl-3,4-dihydro-2H-benzo[b][1,4]dioxepine (6) (1.0 g), ethyl-4-bromobenzoate (1.13 g), $[PdCl_2(PPh_3)_2]$ (174 mg) and copper(I) iodide (94 mg) is added a degassed solution of diisopropylamine (20 ml) and THF (20 ml). The reaction mixture is stirred over night at 57° C. After addition of AcOEt (100 ml) and filtration over dicalite, the solution is washed with 1 N aq. HCl sol. (3×50 ml) and $H_2O$ (3×50 ml). The organic layer is dried over $MgSO_4$ and the solvent is evaporated. The crude product is purified by flash chromatography (silica gel, heptane/AcOEt 9:1) followed by preparative HPLC. 756 mg of 4-(3,3-dimethyl-3,4-dihydro-2H-benzo[b][1,4]dioxepin-7-ylethynyl)-benzoic acid ethyl ester are obtained as a white solid, MS (ESI) 350.2 $(M^{\bullet})^+$.

Example 2

3,3-Dimethyl-7-(4-methylsulfanyl-phenylethynyl)-3,4-dihydro-2H-benzo[b][1,4]dioxepine The title compound is prepared in analogy to example 1 from 7-ethynyl-3,3-dimethyl-3,4-dihydro-2H-benzo[b][1,4]dioxepine (6) (example 1d) and bromothioanisole. MS (ESI) 324.2 $(M^{\bullet})^+$.

Example 3

1-[4-(3,3-Dimethyl-3,4-dihydro-2H-benzo[b][1,4]dioxepin-7-ylethynyl)-phenyl]-ethanone The title compound is prepared in analogy to example 1 from 7-ethynyl-3,3-dimethyl-3,4-dihydro-2H-benzo[b][1,4]dioxepine (6) (example 1d) and 1-(4-iodo-phenyl)-ethanone. MS (ESI) 320.2 $(M^{\bullet})^+$.

Example 4

7-(4-Methoxy-phenylethynyl)-3,3-dimethyl-3,4-dihydro-2H-benzo[b][1,4]dioxepine

The title compound is prepared in analogy to example 1 from 7-ethynyl-3,3-dimethyl-3,4-dihydro-2H-benzo[b][1,4]dioxepine (6) (example 1d) and 1-iodo-4-methoxy-benzene. MS (ESI) 308.2 $(M^{\bullet})^+$.

Example 5

7-(3-Methoxy-phenylethynyl)-3,3-dimethyl-3,4-dihydro-2H-benzo[b][1,4]dioxepine

The title compound is prepared in analogy to example 1 from 7-ethynyl-3,3-dimethyl-3,4-dihydro-2H-benzo[b][1,4]dioxepine (6) (example 1d) and 1-iodo-3-methoxy-benzene. MS (ESI) 308.2 $(M^{\bullet})^+$.

Example 6

4-(3,3-Dimethyl-3,4-dihydro-2H-benzo[b][1,4]dioxepin-7-ylethynyl)-phenol

The title compound is prepared in analogy to example 1 from 7-ethynyl-3,3-dimethyl-3,4-dihydro-2H-benzo[b][1,4]dioxepine (6) (example 1d) and 4-iodo-phenol as a brown solid. MS (ESI) 293.1 $(M-H)^-$.

Example 7

7-(4-Ethoxy-phenylethynyl)-3,3-dimethyl-3,4-dihydro-2H-benzo[b][1,4]dioxepine The title compound is prepared in analogy to example 1 from 7-ethynyl-3,3-dimethyl-3,4-dihydro-2H-benzo[b][1,4]dioxepine (6) (example 1d) and 1-ethoxy-4-iodo-benzene. MS (ESI) 322.2 (M)$^+$.

Example 8

7-Benzo[1,3]dioxol-5-ylethynyl-3,3-dimethyl-3,4-dihydro-2H-benzo[b][1,4]dioxepine The title compound is prepared in analogy to example 1 from 7-ethynyl-3,3-dimethyl-3,4-dihydro-2H-benzo[b][1,4]dioxepine (6) (example 1d) and 5-iodo-benzo[1,3]dioxole. MS (ESI) 322.2 (M)$^+$.

Example 9

7-(2,3-Dihydro-benzofuran-5-ylethynyl)-3,3-dimethyl-3,4-dihydro-2H-benzo[b][1,4]dioxepine The title compound is prepared in analogy to example 1 from 7-ethynyl-3,3-dimethyl-3,4-dihydro-2H-benzo[b][1,4]dioxepine (6) (example 1d) and 5-iodo-2,3-dihydro-benzofuran. MS (ESI) 320.1 (M)$^+$.

Example 10

6-(3,3-Dimethyl-3,4-dihydro-2H-benzo[b][1,4]dioxepin-7-ylethynyl)-nicotinic acid ethyl ester The title compound is prepared in analogy to example 1 from 7-ethynyl-3,3-dimethyl-3,4-dihydro-2H-benzo[b][1,4]dioxepine (6) (example 1d) and ethyl 6-chloro-nicotinate. MS (ESI) 352.4 (M+H)$^+$.

Example 11

7-(4-Ethoxymethyl-phenylethynyl)-3,3-dimethyl-3,4-dihydro-2H-benzo[b][1,4]dioxepine 1-Bromo-4-ethoxymethyl-benzene (16)

A solution of 1.00 g of 4-bromobenzyl bromide in 20 ml EtOH is stirred 5 h under reflux. The solvent is evaporated to obtain 766 mg of 1-bromo-4-ethoxymethyl-benzene as a yellow oil, MS (ESI) 216.1 (M+H)$^+$.

7-(4-Ethoxymethyl-phenylethynyl)-3,3-dimethyl-3,4-dihydro-2H-benzo[b][1,4]dioxepine In analogy to example 1 the title compound is obtained from 7-ethynyl-3,3-dimethyl-3,4-dihydro-2H-benzo[b][1,4]dioxepine (6) (example 1d) and 1-bromo-4-ethoxymethyl-benzene (16) as a white solid. MS (ESI) 336.2 (M)$^+$.

Example 12

2-[4-(3,3-Dimethyl-3,4-dihydro-2H-benzo[b][1,4]dioxepin-7-ylethynyl)-phenyl]-5-methyl-[1,3,4]oxadiazole 2-(4-Iodo-phenyl)-5-methyl-[1,3,4]oxadiazole (19)

A mixture of 4-iodobenzoic acid (1.0 g) and acethydrazide (329 mg) in POCl$_3$ (4 ml) is stirred over night at 80° C., then another day at 100° C. AcOEt (50 ml) is added and the mixture is washed with H$_2$O (50 ml), sat. aq. Na$_2$CO$_3$ sol. (50 ml) and H$_2$O (50 ml). After drying over Na$_2$SO$_4$ the solvent is evaporated and the product is purified by flash chromatography (silica gel, CH$_2$Cl$_2$/MeOH/25% aq. NH$_4$OH 90:9:1). 368 mg of 2-(4-iodo-phenyl)-5-methyl-[1,3,4]oxadiazole (19) are obtained as a yellowish solid, MS (ESI) 287.0 (M+H)$^+$.

2-[4-(3,3-Dimethyl-3,4-dihydro-2H-benzo[b][1,4]dioxepin-7-ylethynyl)-phenyl]-5-methyl-[1,3,4]oxadiazole In analogy to example 1 the title compound is obtained from 7-ethynyl-3,3-dimethyl-3,4-dihydro-2H-benzo[b][1,4]dioxepine (6) (example 1d) and 2-(4-iodo-phenyl)-5-methyl-[1,3,4]oxadiazole as a white solid. MS (ESI) 360.1 (M)$^+$.

Example 13

5-(3,3-Dimethyl-3,4-dihydro-2H-benzo[b][1,4]dioxepin-7-ylethynyl)-pyridine-2-carboxylic acid ethyl ester 5-Bromo-pyridine-2-carboxylic acid ethyl ester (22)

1.17 g of 5-bromo-2-pyridinecarboxylic acid (21), prepared according to G. M. Sanders, M. van Dijk and H. C. van der Plas, *Heterocycles* 1981, 15, 213-223, are placed in SOCl$_2$ (6 ml) and the mixture is heated 2 h under reflux. After evaporation of SOCl$_2$ the residue is treated under reflux with a mixture of toluene (3 ml) and absolute EtOH (6 ml). The pH is adjusted to 8 by addition of sat. aq. Na$_2$CO$_3$ sol. and the product is extracted with Et$_2$O. The organic layer is washed to neutral pH with H$_2$O portions, dried over Na$_2$SO$_4$ and the solvent is evaporated to obtain 377 mg of 5-bromo-pyridine-2-carboxylic acid ethyl ester (22) as a white powder, MS (ESI) 232.0 (M+H)$^+$.

Alternatively 5-bromo-pyridine-2-carboxylic acid ethyl ester (22) can be prepared as described by R. J. Chambers, A. Marfat, *Synthetic Communications* 1997, 27(3), 515-521.

5-(3,3-Dimethyl-3,4-dihydro-2H-benzo[b][1,4]dioxepin-7-ylethynyl)-pyridine-2-carboxylic acid ethyl ester.

The title compound is prepared in analogy to example 1 from 7-ethynyl-3,3-dimethyl-3,4-dihydro-2H-benzo[b][1,4]dioxepine (6) (example 1d) and 5-bromo-pyridine-2-carboxylic acid ethyl ester (22) as a gum. MS (ESI) 351.1 (M)$^+$.

Example 14

5-[4-(3,3-Dimethyl-3,4-dihydro-2H-benzo[b][1,4]dioxepin-7-ylethynyl)-phenyl]-2-methyl-2H-tetrazole 5-(4-Iodo-phenyl)-1H-tetrazole (24)

A mixture of 4-iodobenzonitrile (2.0 g), sodium azide (624 mg) and ammonium chloride (514 mg) in DMF is stirred 22 h at 100° C. DMF is evaporated and the residue is suspended in $H_2O$ and treated with conc. aq. HCl. The solid material is collected by filtration, washed with 1 N aq. HCl sol. and $H_2O$ and dried under high vacuum.

2.32 g of 5-(4-iodo-phenyl)-1H-tetrazole (24) are obtained as a white powder, MS (ESI) 270.9 (M–H)⁻.

5-(4-Iodo-phenyl)-2-methyl-1H-tetrazole (25)

A mixture of 5-(4-iodo-phenyl)-1H-tetrazole (24) (500 mg) and ammonium bromide (1.18 g) in 1 N aq. NaOH sol. (10 ml) and $CH_2Cl_2$ (10 ml) is treated with iodomethane and vigorously stirred 26 h at RT. The organic layer is separated, washed with 1 N aq. NaOH sol., aq. $NH_4Cl$ sol. and brine. After drying over $MgSO_4$ the solvent is evaporated and the product is purified by flash chromatography (silica gel, heptane/$CH_2Cl_2$ 1:1 to pure $CH_2Cl_2$).

387 mg of 5-(4-iodo-phenyl)-2-methyl-2H-tetrazole (25) are obtained as a crystalline white solid, MS (ESI) 286.0 (M⋅)⁺.

105 mg of 5-(4-iodo-phenyl)-1-methyl-1H-tetrazole (26) are obtained as side product, crystalline off-white powder, MS (ESI) 286.0 (M⋅)⁺.

5-[4-(3,3-Dimethyl-3,4-dihydro-2H-benzo[b][1,4]dioxepin-7-ylethynyl)-phenyl]-2-methyl-2H-tetrazole The title compound is obtained in analogy to example 1 from 7-ethynyl-3,3-dimethyl-3,4-dihydro-2H-benzo[b][1,4]dioxepine (6) (example 1d) and 5-(4-iodo-phenyl)-2-methyl-2H-tetrazole (25) as a white powder. MS (ESI) 361.2 (M+H)⁺.

Example 15

3-(3,3-Dimethyl-3,4-dihydro-2H-benzo[b][1,4]dioxepin-7-ylethynyl)-benzoic acid ethyl ester (10)

3-Ethynyl-benzoic acid ethyl ester (9)

The title compound is prepared in analogy to T. Iijima, Y. Endo, M. Tsuji, E. Kawachi, H. Kagechika, K. Shudo, *Chem. Pharm. Bull.* 1999, 47, 3, 398-404).

7-(4-Ethoxymethyl-phenylethynyl)-3,3-dimethyl-3,4-dihydro-2H-benzo[b][1,4]dioxepine To a mixture under $N_2$ of 3-ethynyl-benzoic acid ethyl ester (9) (50 mg), 7-iodo-3,3-dimethyl-3,4-dihydro-2H-benzo[b][1,4]dioxepine (5) (87 mg) (example 1b), [$PdCl_2(PPh_3)_2$] (10 mg) and copper(I) iodide (5.5 mg) is added a degassed mixture of THF (2.5 ml) and diisopropylamine (2.5 ml). After 5.5 h stirring at RT hexane (15 ml) is added and the mixture is washed with 1 N aq. HCl sol. (2×15 ml), $H_2O$ (15 ml) and brine (15 ml). After drying over $MgSO_4$ the solvent is evaporated and the product is purified by flash chromatography (silica gel, hexane/1% AcOEt). 55 mg of 3-(3,3-dimethyl-3,4-dihydro-2H-benzo[b][1,4]dioxepin-7-ylethynyl)-benzoic acid ethyl ester (10) are obtained as a colourless gum, MS (ESI) 350.2 (M⋅)⁺.

Example 16

[4-(3,3-Dimethyl-3,4-dihydro-2H-benzo[b][1,4]dioxepin-7-ylethynyl)-phenyl]-morpholin-4-yl-methanone (4-Iodo-phenyl)-morpholin-4-yl-methanone A mixture of 4-iodobenzoyl chloride (500 mg), morpholine (163 mg) and triethylamine (380 mg) in $CH_2Cl_2$ (20 ml) is stirred 2 h before washing with $H_2O$ (20 ml) and brine (20 ml). The organic layer is dried over $MgSO_4$ and the solvent is evaporated to obtain 482 mg of (4-iodo-phenyl)-morpholin-4-yl-methanone, yellowish semisolid, MS (ESI) 318.0 (M+H)⁺.

Morpholin-4-yl-(4-trimethylsilanylethynyl-phenyl)-methanone

To a mixture under Ar of (4-iodo-phenyl)-morpholin-4-yl-methanone (273 mg), trimethylsilylacetylene (169 mg), [$PdCl_2(PPh_3)_2$] (30 mg) and copper(i) iodide (15 mg) is added a degassed mixture of THF (4.5 ml) and diisopropylamine (4.5 ml). After stirring over night at 57° C. and aqueous work up, the organic layer is dried over $Na_2SO_4$ and the solvent is evaporated. Flash chromatography (silica gel, $CH_2Cl_2$/MeOH/25% $NH_4OH$ 97:3:0.3) yields 247 mg of morpholin-4-yl-(4-trimethylsilanylethynyl-phenyl)-methanone as a light brown solid, ¹H-NMR (300 MHz): 0.26 (s, 3H); 3.32-3.91 (br, 8H); 7.34 (d, J=6.5, 2H); 7.51 (d, J=6.5, 2H).

(4-Ethynyl-phenyl)-morpholin-4-yl-methanone

The material obtained in step b) is treated 1 h at RT with $K_2CO_3$ in a MeOH (30 ml) THF (6 ml) mixture. The reaction mixture is poured on $Et_2O$ (60 ml) and washed with $H_2O$ (2×60 ml). After drying over $Na_2SO_4$ and evaporation of the solvent 110 mg of (4-ethynyl-phenyl)-morpholin-4-yl-methanone are obtained, ¹H-NMR (300 MHz): 3.15 (s, 1H); 3.33-3.94 (br, 8H); 7.37 (d, J=6.6, 2H); 7.53 (d, J=6.6, 2H).

[4-(3,3-Dimethyl-3,4-dihydro-2H-benzo[b][1,4]dioxepin-7-ylethynyl)-phenyl]-morpholin-4-yl-methanone The title compound is prepared in analogy to 3-(3,3-dimethyl-3,4-dihydro-2H-benzo[b][1,4]dioxepin-7-ylethynyl)-benzoic acid ethyl ester (10) from (4-ethynyl-phenyl)-morpholin-4-yl-methanone and 7-iodo-3,3-dimethyl-3,4-dihydro-2H-benzo[b][1,4]dioxepine (5) as a yellow viscous oil, MS (ESI) 392.3 (M+H)⁺.

Example 17

4-(3,3-Dimethyl-3,4-dihydro-2H-benzo[b][1,4]dioxepin-7-ylethynyl)-N,N-dimethyl-benzamide

4-Iodo-N,N-dimethyl-benzamide

The title compound is prepared in analogy to example 16a from 4-iodobenzoyl chloride, N,N-dimethylamine and triethylamine in $CH_2Cl_2$ as a yellowish oil, MS (ESI) 276.0 $(M+H)^+$.

N,N-Dimethyl-4-trimethylsilanylethynyl-benzamide

To a mixture under Ar of 4-Iodo-N,N-dimethyl-benzamide (237 mg), trimethylsilylacetylene (169 mg), $[PdCl_2(PPh_3)_2]$ (30 mg) and copper(i) iodide (15 mg) is added a degassed mixture of THF (4.5 ml) and diisopropylamine (4.5 ml). After stirring over night at 57° C. and aqueous work up, the organic layer is dried over $Na_2SO_4$ and the solvent is evaporated. Flash chromatography (silica gel, $CH_2Cl_2$/MeOH/25% $NH_4OH$ 97:3:0.3) yields N,N-Dimethyl-4-trimethylsilanylethynyl-benzamide as a brown oil, $^1$H-NMR (300 MHz): 0.25 (s, 3H); 2.96 (s, 3H); 3.10 (s, 3H); 7.35 (d, J=8.5, 2H); 7.49 (d, J=8.5, 2H).

4-Ethynyl-N,N-dimethyl-benzamide

The title compound is prepared in analogy to (4-ethynyl-phenyl)-morpholin-4-yl-methanone (Example 16c) from N,N-Dimethyl-4-trimethylsilanylethynyl-benzamide. $^1$H-NMR (300 MHz): 3.15 (s, 1H); 3.33-3.94 (br, 8H); 7.37 (d, J=6.6, 2H); 7.53 (d, J=6.6, 2H).

4-(3,3-Dimethyl-3,4-dihydro-2H-benzo[b][1,4]dioxepin-7-ylethynyl)-N,N-dimethyl-benzamide.

The title compound is prepared in analogy to 3-(3,3-dimethyl-3,4-dihydro-2H-benzo[b][1,4]dioxepin-7-ylethynyl)-benzoic acid ethyl ester (10) from 4-ethynyl-N,N-dimethyl-benzamide and 7-iodo-3,3-dimethyl-3,4-dihydro-2H-benzo[b][1,4]dioxepine (5) as a light brown solid, MS (ESI) 699.4 (100, $[2M+H]^+$), 350.4 (15, $[M+H]^+$).

Example 18

7-(4-Cyclopropylmethoxy-phenylethynyl)-3,3-dimethyl-3,4-dihydro-2H-benzo[b][1,4]dioxepine General procedure for the alkylation of 4-(3,3-dimethyl-3,4-dihydro-2H-benzo[b][1,4]dioxepin-7-ylethynyl)-phenol (Example 6):

4-(3,3-Dimethyl-3,4-dihydro-2H-benzo[b][1,4]dioxepin-7-ylethynyl)-phenol (Example 6) (100 mg) is dissolved in 2 ml DMF and $K_2CO_3$ (141 mg), KI (59 mg) and 1.25 equivalents of the alkyl bromide are added. The mixture is stirred 22 h at 80° C. After cooling to RT $H_2O$ is added and the product is extracted with 3 portions of AcOEt. The combined organic layers are washed with more $H_2O$ and brine and are dried over $Na_2SO_4$. The solvent is evaporated to yield the product.

7-(4-Cyclopropylmethoxy-phenylethynyl)-3,3-dimethyl-3,4-dihydro-2H-benzo[b][1,4]dioxepine is obtained by alkylation with cyclopropylmethyl bromide as a brownish solid, MS (ESI) 349.4 $(M+H)^+$.

Example 19

7-[4-(2-Methoxy-ethoxy)-phenylethynyl]-3,3-dimethyl-3,4-dihydro-2H-benzo[b][1,4]dioxepine The title compound was prepared according to the general procedure described in example 18 by alkylation of 4-(3,3-dimethyl-3,4-dihydro-2H-benzo[b][1,4]dioxepin-7-ylethynyl)-phenol (Example 6) with 2-methoxyethyl bromide as brownish solid, MS (ESI) 353.3 $(M+H)^+$.

Example 20

[4-(3,3-Dimethyl-3,4-dihydro-2H-benzo[b][1,4]dioxepin-7-ylethynyl)-phenoxy]-acetonitrile The title compound was obtained according to the general procedure described in example 18 by alkylation of 4-(3,3-dimethyl-3,4-dihydro-2H-benzo[b][1,4]dioxepin-7-ylethynyl)-phenol (Example 6) with 2-bromo acetonitrile as brownish solid, MS (ESI) 334.3 $(M+H)^+$.

Example 21

3,3-Dimethyl-7-(4-propoxy-phenylethynyl)-3,4-dihydro-2H-benzo[b][1,4]dioxepine The title compound was obtained according to the general procedure described in example 18 by alkylation of 4-(3,3-dimethyl-3,4-dihydro-2H-benzo[b][1,4]dioxepin-7-ylethynyl)-phenol (Example 6) with n-propyl bromide as brownish solid, MS (ESI) 337.4 $(M+H)^+$.

Example 22

3,3-Dimethyl-7-(4-oxiranylmethoxy-phenylethynyl)-3,4-dihydro-2H-benzo[b][1,4]dioxepine The title compound was obtained according to the general procedure described in example 18 by alkylation of 4-(3,3-dimethyl-3,4-dihydro-2H-benzo[b][1,4]dioxepin-7-ylethynyl)-phenol (Example 6) with epibromohydrin as brownish solid, MS (ESI) 351.4 $(M+H)^+$.

Example 23

4-(3,3-Dimethyl-3,4-dihydro-2H-benzo[b][1,4]dioxepin-7-ylmethoxy)-benzoic acid ethyl ester

2,2-Dimethyl-1,3-propanediole ditosylate (2)

The title compound is prepared according to the method described in R. Bird, G. Griffiths, G. F. Griffiths, C. J. M. Stirling, *J. Chem. Soc. Perkin Trans.* 2, 1982, 579 or according to M. Klaus, P. Mohr, E. Weiss, Eur. Pat. Appl. EP 0 350 846 A2 (1990).

3,3-Dimethyl-3,4-dihydro-2H-benzo[b][1,4]dioxepine-7-carboxylic acid ethyl ester (30)

Ethyl-3,4-dihydroxybenzoate (20.0 g) is dissolved in DMF (300 ml) and the solution is heated to 40° C. After addition of $K_2CO_3$ the mixture is stirred 1 h at the same temperature before addition of 2,2-dimethyl-1,3-propanediole ditosylate (49.9 g,) in DMF (240 ml). The mixture is stirred 5 h at 140° C., then is poured on ice and the product is extracted with $Et_2O$. The organic layer is washed with $H_2O$, dried over MgSO$_4$ and the solvent is evaporated. Distillation (126° C., 0.5 mbar) yields 19.8 g of 3,3-dimethyl-3,4-dihydro-2H-benzo[b][1,4]dioxepine-7-carboxylic acid ethyl ester (30) as a colourless liquid, MS (ESI) 250.1 (M$^{\cdot}$)$^+$.

(3,3-Dimethyl-3,4-dihydro-2H-benzo[b][1,4]dioxepin-7-yl)-methanol (31)

3,3-Dimethyl-3,4-dihydro-2H-benzo[b][1,4]dioxepine-7-carboxylic acid ethyl ester (30) (9.00 g) is dissolved in THF (150 ml) and a 1.5 M solution of diisobutylaluminium hydride in toluene (120 ml) is slowly added. The resulting reaction mixture is stirred 1 h at RT, then cooled to −30° C. and H$_2$O (120 ml) is cautiously added. After letting the temperature rise to RT a 20% aq. HCl solution (100 ml) is added. The ether layer is collected, washed with H$_2$O and dried over Na$_2$SO$_4$ and the solvent is evaporated. Flash chromatography (silica gel, hexane/AcOEt 4:1) yields 7.25 g of (3,3-dimethyl-3,4-dihydro-2H-benzo[b][1,4]dioxepin-7-yl)-methanol (31), MS (ESI) 208.1 (M$^{\cdot}$)$^+$.

4-(3,3-Dimethyl-3,4-dihydro-2H-benzo[b][1,4]dioxepin-7-ylmethoxy)-benzoic acid ethyl ester To a mixture of (3,3-dimethyl-3,4-dihydro-2H-benzo[b][1,4]dioxepin-7-yl)-methanol (31) (100 mg), polymer bound PPh$_3$ (412 mg, ~3 mmol/g on polystyrene) and ethyl-4-hydroxybenzoate in CH$_2$Cl$_2$ (4 ml) is added di-tert-butylazodicarboxylate (111 mg). The mixture is shaken 1 h, then the polymer is filtered off and the solvent is evaporated. Flash chromatography yields 74 mg of 4-(3,3-dimethyl-3,4-dihydro-2H-benzo[b][1,4]dioxepin-7-ylmethoxy)-benzoic acid ethyl ester as a colourless oil, MS (ESI) 357.2 (M+H)$^+$.

Example 24

7-(4-Isopropyl-phenoxymethyl)-3,3-dimethyl-3,4-dihydro-2H-benzo[b][1,4]dioxepine In analogy to the method described in example 23, 7-(4-isopropyl-phenoxymethyl)-3,3-dimethyl-3,4-dihydro-2H-benzo[b][1,4]dioxepine is prepared from (3,3-dimethyl-3,4-dihydro-2H-benzo[b][1,4]dioxepin-7-yl)-methanol (31) and 4-isopropylphenol. MS (ESI) 344.4 (M+NH$_4$)$^+$.

Example 25

3,3-Dimethyl-7-(4-methylsulfanyl-phenoxymethyl)-3,4-dihydro-2H-benzo[b][1,4]dioxepine According to the method described in example 23, the title compound is prepared from (3,3-dimethyl-3,4-dihydro-2H-benzo[b][1,4]dioxepin-7-yl)-methanol (31) and 4-(methylthio)phenol. MS (ESI) 331.3 (M+H)$^+$.

Example 26

7-(3-Ethoxy-phenoxymethyl)-3,3-dimethyl-3,4-dihydro-2H-benzo[b][1,4]dioxepine

According to the method described in example 23, the title compound is obtained from (3,3-dimethyl-3,4-dihydro-2H-benzo[b][1,4]dioxepin-7-yl)-methanol (31) and 3-ethoxyphenol. MS (ESI) 346.2 (M+NH$_4$)$^+$.

Example 27

7-(4-Ethyl-phenoxymethyl)-3,3-dimethyl-3,4-dihydro-2H-benzo[b][1,4]dioxepine

According to the method described in example 23, 7-(4-ethyl-phenoxymethyl)-3,3-dimethyl-3,4-dihydro-2H-benzo[b][1,4]dioxepine is obtained from (3,3-dimethyl-3,4-dihydro-2H-benzo[b][1,4]dioxepin-7-yl)-methanol (31) and 4-ethylphenol. MS (ESI) 346.2 (M+NH$_4$)$^+$.

Example 28

7-(4-Methoxy-phenoxymethyl)-3,3-dimethyl-3,4-dihydro-2H-benzo[b][1,4]dioxepine

According to the method described in example 23, the title compound is prepared from (3,3-dimethyl-3,4-dihydro-2H-benzo[b][1,4]dioxepin-7-yl)-methanol (31) and 4-methoxyphenol. MS (ESI) 332.3 (M+NH$_4$)$^+$.

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

Example C

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| | |
|---|---|
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

The invention claimed is:

1. A compound of the formula

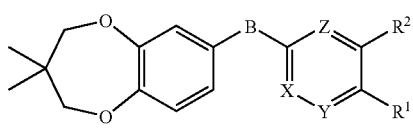

wherein

B is —C≡C— or —CHR$^3$—O—;

R$^3$ is H or C$_{1-3}$-alkyl;

X, Y and Z are C—R$^4$;

R$^4$ is H or C$_{1-7}$-alkyl; and wherein R$^1$ or R$^2$ is selected from the group consisting of C$_{1-7}$-alkyl, C$_{1-7}$-alkoxy-C$_{1-7}$-alkyl, —COOR$^5$, wherein R$^5$ is H or C$_{1-7}$-alkyl, —OR$^6$, wherein R$^6$ is H, C$_{1-7}$-alkyl, —(CH$_2$)$_m$-cycloalkyl, —(CH$_2$)$_n$—CN, or —(CH$_2$)$_n$—OR$^7$, and R$^7$ is H or C$_{1-7}$-alkyl, wherein m is 0, 1, 2 or 3 and n is 1, 2 or 3; and —SR$^8$, wherein R$^8$ is C$_{1-7}$-alkyl;

or the pharmaceutically acceptable salts thereof.

2. The compound of claim 1, wherein R$^1$ or R$^2$ is —COOR$^5$, and R$^5$ is H or C$_{1-7}$-alkyl.

3. The compound of claim 1, wherein one of R$^1$ or R$^2$ is hydrogen and the other is selected from the group consisting of C$_{1-7}$-alkoxy-C$_{1-7}$-alkyl, —OR$^6$, wherein R$^6$ is H, C$_{1-7}$-alkyl, —(CH$_2$)$_m$-cycloalkyl, —(CH$_2$)$_n$—CN, or —(CH$_2$)$_n$—OR$^7$, and R$^7$ is H or C$_{1-7}$-alkyl, wherein m is 0, 1, 2 or 3 and n is 1, 2 or 3; and —SR$^8$, wherein R$^8$ is C$_{1-7}$-alkyl.

4. The compound of claim 1 having the formula

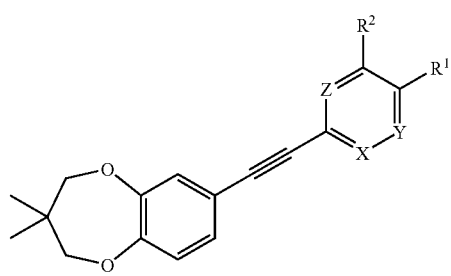

wherein

X, Y, Z, R$^1$ and R$^2$ are as defined in claim 4; or the pharmaceutically acceptable salt thereof.

5. The compound of claim 4 selected from the group consisting of 4-(3,3-dimethyl-3,4-dihydro-2H-benzo[b][1,4]dioxepin-7-ylethynyl)-benzoic acid ethyl ester;

3-(3,3-dimethyl-3,4-dihydro-2H-benzo[b][1,4]dioxepin-7-ylethynyl)-benzoic acid ethyl ester;

3,3-dimethyl-7-(4-methylsulfanyl-phenylethynyl)-3,4-dihydro-2H-benzo[b][1,4]dioxepine;

7-(4-methoxy-phenylethynyl)-3,3-dimethyl-3,4-dihydro-2H-benzo[b][1,4]dioxepine;

4-(3,3-dimethyl-3,4-dihydro-2H-benzo[b][1,4]dioxepin-7-ylethynyl)-phenol;

7-(4-ethoxy-phenylethynyl)-3,3-dimethyl-3,4-dihydro-2H-benzo[b][1,4]dioxepine;

7-(4-ethoxymethyl-phenylethynyl)-3,3-dimethyl-3,4-dihydro-2H-benzo[b][1,4]dioxepine;

7-(4-cyclopropylmethoxy-phenylethynyl)-3,3-dimethyl-3,4-dihydro-2H-benzo[b][1,4]dioxepine;

3,3-dimethyl-7-(4-propoxy-phenylethynyl)-3,4-dihydro-2H-benzo[b][1,4]dioxepine; and 3,3-dimethyl-7-(4-oxiranylmethoxy-phenylethynyl)-3,4-dihydro-2H-benzo[b][1,4]dioxepine.

6. The compound of claim 1 having the formula

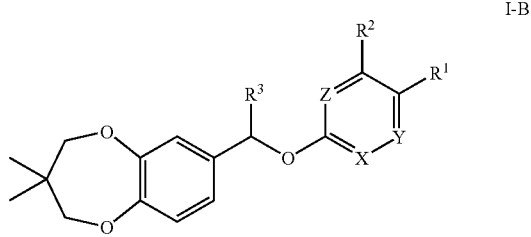

I-B wherein

X, Y, Z, $R^1$, $R^2$ and $R^3$ are as defined in claim 1; or the pharmaceutically acceptable salt thereof.

7. The compound of claim 6 selected from the group consisting of 4-(3,3-dimethyl-3,4-dihydro-2H-benzo[b][1,4]dioxepin-7-ylmethoxy)-benzoic acid ethyl ester; and 7-(3-ethoxy-phenoxymethyl)-3,3-dimethyl-3,4-dihydro-2H-benzo[b][1,4]dioxepine.

8. A pharmaceutical composition comprising a pharmacologically effective amount of a compound according to claim 1 and a pharmaceutically acceptable carrier and/or adjuvant.

9. A method for the treatment of diabetes, obesity or dyslipidemia comprising administering an effective amount of the pharmaceutical composition of claim 8.

10. The method of claim 9 wherein the diabetes is non-insulin dependent diabetes mellitus.

* * * * *